United States Patent
Hudon

(10) Patent No.: US 7,156,825 B2
(45) Date of Patent: Jan. 2, 2007

(54) SAFETY ADAPTER FOR NEEDLE HUB ASSEMBLY

(75) Inventor: Lawrence P. Hudon, Hinsdale, NH (US)

(73) Assignee: Smiths Medical ASD, Inc., Keene, NH (US)

(*) Notice: Subject to any disclaimer, the term of this patent is extended or adjusted under 35 U.S.C. 154(b) by 503 days.

(21) Appl. No.: 10/391,794

(22) Filed: Mar. 20, 2003

(65) Prior Publication Data
US 2004/0186438 A1  Sep. 23, 2004

(51) Int. Cl.
*A61M 5/32* (2006.01)
*A61M 5/00* (2006.01)

(52) U.S. Cl. ..................... 604/192; 604/263
(58) Field of Classification Search ........ 604/192–198, 604/110, 263, 187, 164.08, 162; 128/919
See application file for complete search history.

(56) References Cited

U.S. PATENT DOCUMENTS

| | | | |
|---|---|---|---|
| 4,664,259 A | 5/1987 | Landis | |
| 4,982,842 A | 1/1991 | Hollister | |
| 5,154,285 A | 10/1992 | Hollister | |
| 5,232,454 A | 8/1993 | Hollister | |
| 5,277,311 A | 1/1994 | Hollister | |
| 5,490,841 A * | 2/1996 | Landis | ........................ 604/110 |
| 5,681,295 A * | 10/1997 | Gyure et al. | ................. 604/263 |
| 6,695,819 B1 * | 2/2004 | Kobayashi | .................. 604/192 |

* cited by examiner

*Primary Examiner*—Manuel Mendez
*Assistant Examiner*—Matthew F. DeSanto
(74) *Attorney, Agent, or Firm*—Louis Woo

(57) ABSTRACT

To retrofit a conventional needle hub assembly with a needle protection housing, a sleeve having a collar rotatably fitted thereabout is fitted to the needle hub. The sleeve has a proximal portion and a distal portion. The proximal portion has a diameter that is dimensioned to fit over the needle hub while the distal portion has a diameter that allows the needle cap of the needle hub assembly to be inserted thereinto so as to be frictionally coupled to the needle hub. There are a plurality of flanges or ears extending at the proximal end of the proximal portion. These flanges are configured to overlie the flanges formed at the base of the needle hub used to mate with the luer of a syringe. When the needle hub assembly is threadingly mated to the luer of the syringe, the sleeve, along with the collar mounted thereabout and to which the needle protection housing is attached, is also mated to the luer. As a consequence, a conventional needle hub assembly could be retrofitted with the inventive sleeve assembly without causing any dead space which may unnecessarily waste to be dispensed medicament and/or collected patient fluid.

21 Claims, 2 Drawing Sheets

SAFETY ADAPTER FOR NEEDLE HUB ASSEMBLY

FIELD OF THE INVENTION

The present invention relates to a needle protection device and more particularly to an adapter that is fitted to a conventional needle hub assembly so that the assembly may be retrofitted with or added thereto a needle protection device when it is used with a syringe.

BACKGROUND OF THE INVENTION

To prevent a contaminated needle from being exposed, needle protection housings are used. U.S. Pat. No. 4,982,842 discloses an adapter to which a needle hub assembly and a syringe are mated. A needle protection housing is hingedly connected to the adapter so that the housing may be pivoted to cover the needle extending from the needle hub once it has been used. The needle housing for the adapter of the '842 patent is not rotatable. U.S. Pat. No. 5,277,311 discloses a housing attached to a collar, with the collar mounted about the neck of a Vacutainer holder, so that the housing is rotatable with respect to a double ended needle mated to the Vacutainer holder. U.S. Pat. No. 5,681,295 discloses a needle hub especially made to include a collar receiving recess so that a collar may be fitted directly about the needle hub. A needle protection housing is connected to the collar.

SUMMARY OF THE PRESENT INVENTION

The present invention allows the retrofitting of a needle protection housing to a conventional needle hub assembly, without the disadvantages of the prior art which requires, among other things, the design of a special needle hub. To achieve this end, the safety device of the instant invention has a sleeve that is adaptable to fit over a conventional needle hub. The sleeve has a proximal portion that is dimensioned to fit to the hub of a conventional needle assembly. The sleeve also has a distal portion that has an opening dimensioned to allow the needle cap or sheath of a conventional needle assembly to pass through so that the base of the cap would frictionally couple to the hub of the needle assembly, thereby covering the needle before its use. A groove or recess is formed at the outer surface of the distal portion of the sleeve to allow a collar or ring to rotatably mount thereabout. Attached to the collar, by way of a living hinge, is a needle protection sheath or housing, which may have at least one integral hook formed therein.

To use a needle assembly outfitted with the above disclosed sleeved housing, the cap protecting the needle is removed, and the needle protection housing is rotated to an appropriate orientation so that the user can view clearly the tip of the needle for insertion to the patient. After use and after the withdrawal of the needle from the patient, the user only needs to pivot the needle protection housing into an alignment position with respect to the longitudinal axis of the sleeve, or the needle hub assembly, so that the needle protection housing covers the needle. Once covered by the housing and held by the internal hook of the housing, the needle is no longer removable from the needle protection housing. The syringe could then be discarded.

In an alternative embodiment of the invention, instead of an internal hook in the needle protection housing, openings or apertures may be provided at the lower portion of the housing that matingly latch with locking members formed at either the distal portion of the sleeve, or the collar of the housing, so that when the needle protection housing is pivoted to cover the needle, the openings at the base of the housing will coact with the locking member at the sleeve or the collar to fixedly retain the needle protection housing in the alignment position to ensure that the needle is securely covered. The second embodiment may be combined with the first embodiment in that both integral hook(s) and side locking members may be provided to retain the needle protection housing in place to cover the contaminated needle.

DETAILED DESCRIPTION OF THE INVENTION

Figure 1:
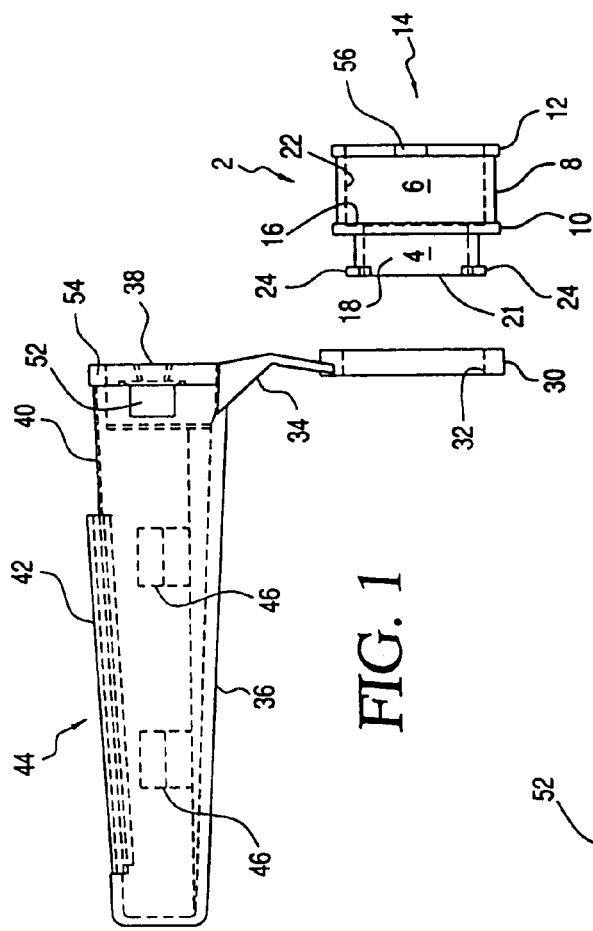
FIG. 1 is a side view of the sleeve assembly of the instant invention.
Figure 2:
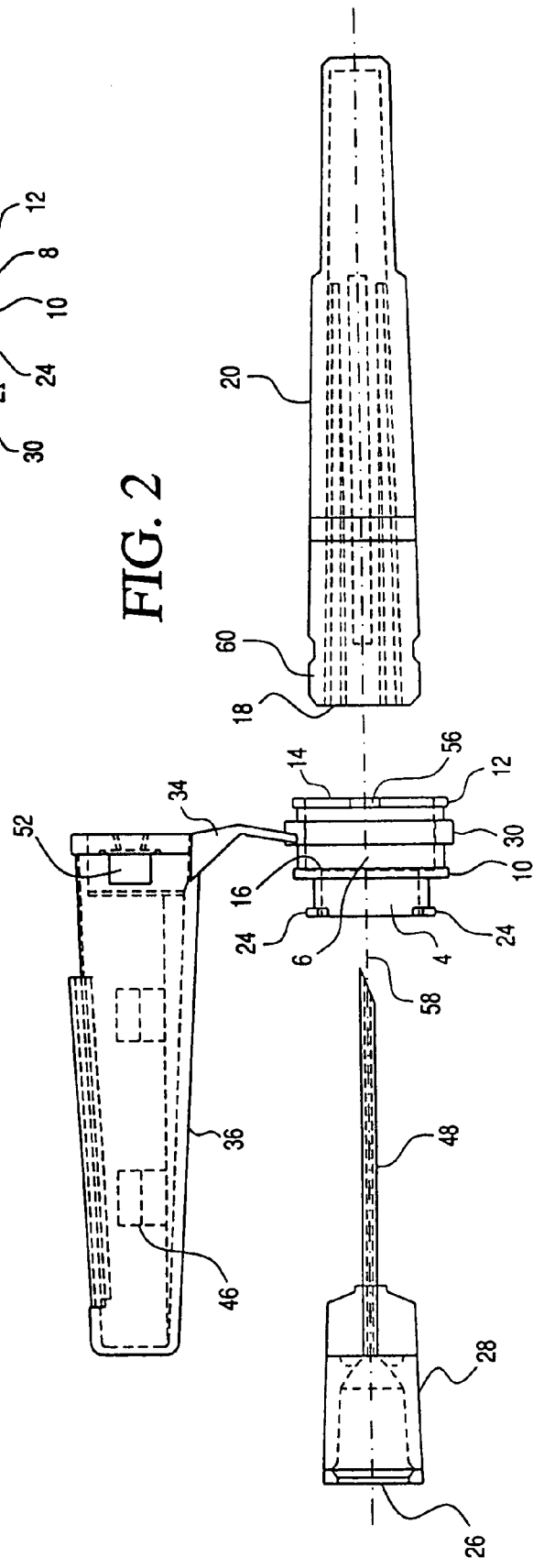
FIG. 2 is a side view of the inventive sleeve assembly in relationship to a conventional needle hub assembly.

With reference to FIG. 1, the sleeve assembly of the instant invention is shown to include a sleeve 2 having a proximal section 4 and a distal portion 6. The distal portion is shown to have a groove or recess 8 bounded by two raised ends 10 and 12. The sleeve is cylindrical and has a through bore indicated by directional arrow 14. At the intersection of the proximal portion 4 and the distal portion 6 there is an internal circumferential shoulder 16 onto which the base 18 of a needle sheath or cap 20 abuts, when inserted to the opening indicated by directional arrow 14. Proximal section 4 has a first internal diameter 18, indicated by the dotted lines extending from the intersection of the proximal portion 4 and the distal portion 6, and a proximal opening 21. Distal portion 6 has an internal diameter 22 that is larger than diameter 18 of the proximal portion 4. Ears or flanges 24 are provided at the base of proximal portion 4. These flanges are designed to overlay, or superpose, over the flanges or ears 26 of the needle hub 28 of the needle hub assembly shown in FIGS. 2 and 3.

A collar or ring 30 is fitted to sleeve 2 about groove 8. Collar 30 has an internal diameter 32 that is slightly wider than the diameter of recess 8 so as to enable it to rotate relative to sleeve 2. Collar 30 is able to be press fit to groove 8 since both collar 30 and sleeve 2 are made of a plastic material such as polypropylene that has certain elastic characteristics that allow the collar to stretch over raised end 10 and then return to its original shape, when collar 30 is mounted about groove 8. Although shown in the drawings to have a width narrower than the width of recess 8, it should be appreciated that collar 30 may actually have a width that allows it to fully seat about groove 8.

Attached to collar 30, by way of a living hinge 34, is a needle protection housing 36. The needle protection housing 36 is exemplified by the housing that is disclosed in the aforementioned '842 patent, the disclosure of which is incorporated by reference herein. In particular, housing 36 may be made of the same material as collar 30 and is substantially cylindrical in shape. At its bottom 38, housing 36 is open. An elongate slot 40 extends from opening 38 to the distal portion of housing 36. Slot 40 may be covered by a trap door 42, which may open in the direction as indicated by directional arrow 44, but could not be opened in the reverse direction.

Figure 4:
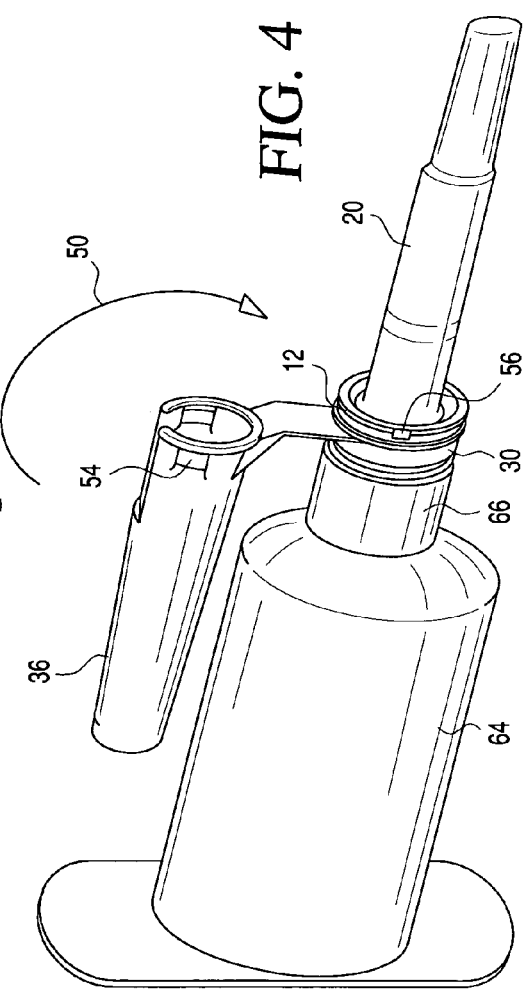
FIG. 4 is a perspective view of a needle hub assembly outfitted with the sleeve assembly of the instant invention mated with a syringe.

Alternatively or in addition, a plurality of needle latching mechanisms such as hooks 46 are integrated to housing 36 for grasping a needle such as needle 48 that extends from needle hub 28, when housing 36 is pivoted in the direction as indicted by directional arrow 50 (FIG. 4) to cover needle 48, assuming that needle cap 20 shown in FIG. 4 has been removed and needle 48 is exposed. There may also be formed apertures or openings 52 at the base 54 of housing 36. Apertures 52 will coact with fingers 56 formed at the distal end of distal portion 6, or on collar 30. Finger 56 and its opposite member on the other side of sleeve 2 would extend into aperture 52 and latch onto base 54, when housing 36 is pivoted along the direction indicated by arrow 50 to be in alignment along the longitudinal axis 58 of sleeve 2 or the needle hub assembly, when housing 36 is moved to cover needle 48.

Figure 3:
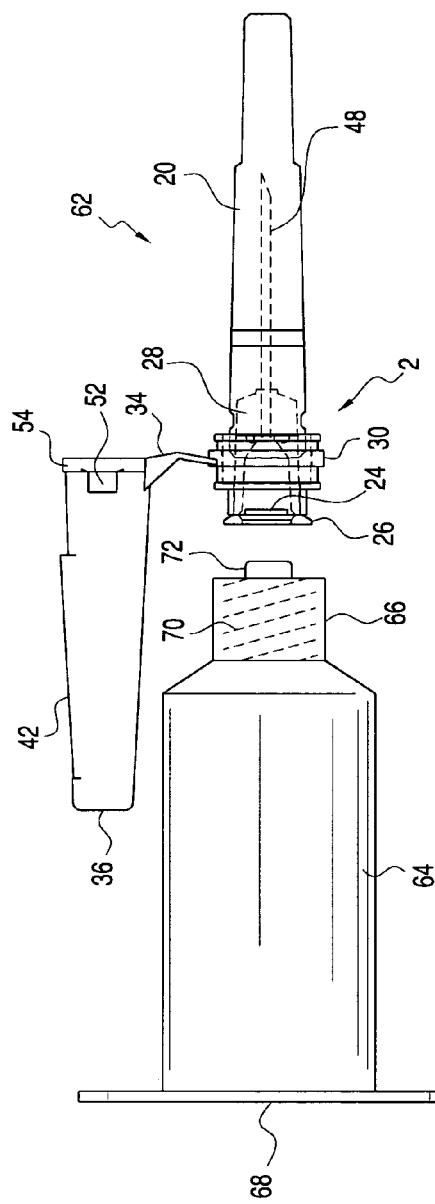
FIG. 3 is a side view of a needle hub assembly outfitted with the sleeve assembly of the instant invention about to be mated to a conventional syringe shown without its plunger.

As discussed above, the opening 14 of distal portion 6 is dimensioned to have a diameter sufficiently large to enable needle cap 20, or more precisely the base portion 60 of the cap, to insert thereinto so that base portion 60 is frictionally coupled to needle hub 28. As shown in FIG. 3, sleeve 2 has been fitted about needle hub 28. Once frictionally coupled to needle 28, since base portion 60 of needle cap 20 has a diameter that is larger than the internal shoulder 16 formed by the intersection of distal portion 6 and proximal portion 4 of sleeve 2, the sleeve assembly is held fixedly by the needle hub 28 coupled with needle cap 20. Thus, the combination sleeve assembly and needle hub assembly as shown per assembled in FIG. 3, after sterilization, can be shipped as one unit.

The unit thus assembled, designated 62, has a sleeve 2 that is rotatable about the needle hub 28. At the same time, collar 30, which is mounted about sleeve 2, is rotatable about sleeve 2, subject to a force applied thereagainst, as the tolerances of the outer circumference of groove 8 and the inner diameter 32 of the collar are such that collar 30 is not freely rotatable about sleeve 2. Housing 36 therefore would remain at a given orientation with respect to needle 48, once the torque forced is removed.

As shown in FIG. 3, the assembled unit of sleeve assembly/needle hub assembly is used with a fluid collecting or dispensing container such as a syringe 64. Syringe 64 has at one end a luer connector 66, or simply luer, and at the other end an opening 68 for accepting a plunger, not shown. Luer 66, as conventionally known, is internally threaded. The internal groove 70 is configured to accept flange or lip 26 of needle hub 28, so that as needle hub 28 threadedly mates with luer 66, the male portion 72 of luer 66 is inserted into the cavity of needle hub 28 to establish a through passage between needle 48 and syringe 64. As flange 26 is being threaded to luer 66, given that flange 24 of sleeve 2 overlies flange 26, sleeve 2 likewise is threadedly mated to luer 66. As a consequence, before use, a syringe could be fitted with a combination sleeve assembly and needle hub assembly of the instant invention, per shown in FIG. 4.

To use, needle cap 20 is removed. Thereafter, the phlebotomist would insert needle 48 to the patient. After the medicament in syringe 64 has been infused to the patient or blood (or other fluid) withdrawn from the patient, needle 48 is withdrawn and housing 36 is pivoted along the direction indicated by directional arrow 50 to cover the contaminated needle. Depending on the embodiment of housing 36, the needle could snap over the trap door 32 and be trapped within the interior of housing 36. Alternatively or in addition thereto, the needle could be grasped by hooks 46, as it snaps past the tips of hooks 46.

In place of, or in addition to hooks 46, the locking mechanism provided by the combination of apertures 52 and catches 56 enables housing 36 to be retained at the alignment position, once pivoted to that position, to cover the contaminated needle 48. To ensure that each of apertures 54 coacts with a corresponding catch 56, a plurality of catches 56 may be formed about the distal lip 12 of distal portion 6 so that no matter the orientation of housing 36 with respect to the tip of the needle 48, when pivoted to the alignment position per the direction indicated by directional arrow 50, apertures 52 are guaranteed to coact with corresponding catches 56. Ounce securely covered, the contaminated needle, and the syringe, may be discarded.

By retrofitting a conventional needle hub assembly with the inventive sleeve assembly, an inexpensive needle protection device that allows rotation of a needle protection housing relative to the needle is provided. At the same time, the configuration of the needle hub need not be altered. Further, no medicament is wasted in the case of the syringe being used for dispensing fluid to the patient, as the inventive sleeve does not affect the size or shape of the conventional needle hub. The same is true when a syringe is used to withdraw fluid from the patient in that no withdrawn fluid needs to be wasted. As a consequence, the inventive sleeve assembly is not affected by any dead space issue when dispensing fluid to or withdrawing fluid from a patient.

The invention claimed is:

1. A needle protection device, comprising:
   a sleeve removably fittable about a needle hub wherefrom a needle extends, said sleeve having at least one flange that overlies a flange extending from the proximal end of said needle hub; and
   a ring rotatably mounted about said sleeve;
   a needle protective housing attached to said ring;
   wherein said sleeve is threadedly mated to a luer of a fluid collecting or dispensing container so as to be fixedly coupled thereto at the same time with said needle hub or after said needle hub has been threadedly mated to said luer while said needle protective housing is rotatable about said sleeve, said needle protective housing pivotable toward said needle hub for covering said needle.

2. Needle protection device of claim 1, further comprising:
   a sheath for capping said needle prior to its use, said sheath mated to said needle hub after said sleeve has been fitted about said needle hub, said sheath removable from said needle hub after said hub is mated to said luer, said sleeve remaining mated to said luer after the removal of said sheath.

3. Needle protection device of claim 1, wherein said sleeve comprises a proximal portion having a first diameter that enables it to fit over said needle hub and a distal portion having a second diameter larger than said first diameter, an internal circular ledge formed by the intersection of said proximal and distal portions, said distal portion accepting the proximal end of a sheath for capping said needle, the bottom surface of the proximal end of said sheath abutting said ledge when said sheath caps said needle and couples to said hub.

4. Needle protection device of claim 1, wherein said sleeve comprises a groove and wherein said ring is rotatably mounted to said sleeve about said groove.

5. Needle protection device of claim 1, wherein said housing includes at least one internal hook for retaining said needle when said housing is pivoted to cover said needle.

6. Needle protection device of claim 1, wherein said housing comprises one part of a latching mechanism at its proximal end that coacts against an other part of said latching mechanism at either said ring or said sleeve so that when said housing is pivoted to cover said needle, said one and other parts of said latching mechanism interact to prevent said housing from pivoting away from said needle.

7. Needle protection device of claim 1, wherein said container comprises a syringe.

8. Needle protection device of claim 1, wherein said housing comprises an elongate one way door that opens when acted against by said needle when said housing is pivoted to cover said needle, but will not open when acted by said needle from inside said housing.

9. Apparatus for use with a syringe, comprising:

a cylindrical sleeve having a distal portion and a proximal portion, the proximal portion having a flange and having a first diameter dimensioned to fit about the hub of a needle hub and the distal portion having a second diameter dimensioned to allow a sheath to cap a needle by extending into said distal portion, said sheath having a proximal opening dimensioned to frictionally couple to said needle hub when said sheath caps said needle, said sleeve including a groove formed about said distal portion, a ring having connected thereto a needle protective housing being rotatably mounted about said groove, said proximal portion of said sleeve and said needle hub adaptable to threadedly mate with a luer end of a syringe, wherein once mated to said syringe said sleeve and said needle hub are fixedly coupled to the luer end of said syringe while said needle protective housing is rotatable about said sleeve.

10. Apparatus of claim 9, wherein said sleeve comprises at least one flange formed at its proximal portion to enable said sleeve to be threadedly mated to the luer end of said syringe along with said needle hub.

11. Apparatus of claim 9, wherein said sleeve comprises at least one lock part formed at the distal portion of said sleeve or said ring for latching with an other lock part formed at said housing as said housing is pivoted toward said needle to cover said needle, wherein, once latched, said lock parts prevent said housing from being pivoted away from said needle.

12. Apparatus of claim 9, wherein said housing comprises at least one integral hook for retaining said needle when said housing is pivoted toward said needle and reaches a position that covers said needle.

13. Apparatus of claim 9, wherein said housing comprises an elongate one way door that opens when acted against by said needle when said housing is pivoted to cover said needle, but will not open when acted by said needle from inside said housing.

14. A needle assembly, comprising:

a needle attached to a needle hub, said needle hub having at least one flange for threadingly mating with a luer of a fluid collecting or dispensing container;

a sleeve mounted about said needle hub, said sleeve having at least one flange that superposes over the flange of said needle hub, said sleeve being threaded to said luer together with said needle hub;

a ring rotatably coupled about said sleeve; and a needle protective housing attached to said ring;

wherein after said needle hub and said sleeve are mated to said luer, said housing is rotatable about said sleeve and pivotable to a position in alignment with said needle for covering said needle.

15. Needle assembly of claim 14, further comprising:

a sheath for capping said needle prior to its use, said sheath mated to said needle hub after said sleeve has been fitted about said needle hub, said sheath removable from said needle hub after said hub is mated to said luer.

16. Needle assembly of claim 14, wherein said sleeve comprises a proximal portion having a first diameter that enables it to mount to said needle hub and a distal portion having a second diameter larger than said first diameter, an internal circular ledge formed by the intersection of said proximal and distal portions, said distal portion accepting the proximal end of a sheath for capping said needle, the bottom surface of the proximal end of said sheath abutting said ledge when said sheath caps said needle and couples to said hub.

17. Needle assembly of claim 14, wherein said sleeve comprises a groove formed at its distal portion, and wherein said ring is rotatably mounted to said sleeve about said groove.

18. Needle assembly of claim 14, wherein said housing includes at least one internal hook for retaining said needle when said housing is pivoted to cover said needle.

19. Needle assembly of claim 14, wherein said housing comprises one part of a latching mechanism at its proximal end that coacts against an other part of said latching mechanism at either said ring or said sleeve so that when said housing is pivoted to cover said needle, said one and other parts of said latching mechanism interact to prevent said housing from pivoting away from said needle.

20. Needle assembly of claim 14, wherein said container comprises a syringe.

21. Needle assembly of claim 14, wherein said housing comprises an elongate one way door that opens only when acted against by said needle when said housing is pivoted to cover said needle.

\* \* \* \* \*